US011923091B2

(12) United States Patent
Schler et al.

(10) Patent No.: US 11,923,091 B2
(45) Date of Patent: Mar. 5, 2024

(54) METHODS FOR REMOTE VISUAL IDENTIFICATION OF CONGESTIVE HEART FAILURES

(71) Applicants: Baruch Schler, Petach Tikwa (IL); Jonathan Schler, Petach Tikwa (IL)

(72) Inventors: Baruch Schler, Petach Tikwa (IL); Jonathan Schler, Petach Tikwa (IL)

( * ) Notice: Subject to any disclaimer, the term of this patent is extended or adjusted under 35 U.S.C. 154(b) by 0 days.

(21) Appl. No.: 18/045,700

(22) Filed: Oct. 11, 2022

(65) Prior Publication Data

US 2023/0059768 A1   Feb. 23, 2023

Related U.S. Application Data

(60) Continuation-in-part of application No. 17/649,452, filed on Jan. 31, 2022, now Pat. No. 11,744,464, (Continued)

(51) Int. Cl.
*G16H 50/20* (2018.01)
*A61B 5/00* (2006.01)
(Continued)

(52) U.S. Cl.
CPC .......... *G16H 50/20* (2018.01); *A61B 5/4082* (2013.01); *A61B 5/4088* (2013.01); *G06N 3/044* (2023.01); *G06N 3/08* (2013.01); *G06V 10/40* (2022.01); *G16H 30/40* (2018.01); *G16H 40/67* (2018.01); *G16H 50/30* (2018.01)

(58) Field of Classification Search
CPC ........ G16H 50/20; G16H 30/40; G16H 40/67; G16H 50/30; A61B 5/4082; A61B 5/4088; G06N 3/0445; G06N 3/08; G06V 10/40
See application file for complete search history.

(56) References Cited

U.S. PATENT DOCUMENTS 9,839,699 B2   12/2017   Koronyo et al.
2008/0242950 A1   10/2008   Jung et al.
(Continued)

FOREIGN PATENT DOCUMENTS

CN   110674773 A   1/2020
KR   20170001106 A   1/2017
(Continued)

OTHER PUBLICATIONS

"Eyes Reveal Early Alzheimer's Disease," by Northwestern University, 2019, pp. 1-2, Science Daily.
(Continued)

*Primary Examiner* — Tom Y Lu
(74) *Attorney, Agent, or Firm* — M&B IP Analysts, LLC

(57) ABSTRACT

A method and system for remote diagnosis of a congestive heart failure in humans is presented. The method includes receiving a facial image of a patient, wherein the facial image is retrieved from a data store and captured from the patient; extracting, from the facial image, at least one facial feature indicative of a heart condition; classifying the extracted at least one facial feature using a classifier, wherein the classifier maps a plurality of candidate facial features to a plurality of scores indicating a stage of the heart condition; and determining a positive diagnosis and the stage of the heart condition of the patient based on the plurality of scores.

20 Claims, 6 Drawing Sheets

Related U.S. Application Data which is a division of application No. 16/880,683, filed on May 21, 2020, now Pat. No. 11,276,498.

(51) Int. Cl.

| | |
|---|---|
| *G06N 3/044* | (2023.01) |
| *G06N 3/08* | (2023.01) |
| *G06V 10/40* | (2022.01) |
| *G16H 30/40* | (2018.01) |
| *G16H 40/67* | (2018.01) |
| *G16H 50/30* | (2018.01) |

(56) References Cited

U.S. PATENT DOCUMENTS

| | | | |
|---|---|---|---|
| 2014/0172310 A1* | 6/2014 | Chin | G16Z 99/00 702/19 |
| 2017/0251985 A1 | 9/2017 | Howard | |
| 2017/0258390 A1 | 9/2017 | Howard | |
| 2018/0289334 A1* | 10/2018 | De Brouwer | G06V 40/169 |
| 2018/0325441 A1 | 11/2018 | Deluca et al. | |
| 2019/0110754 A1 | 4/2019 | Rao et al. | |
| 2020/0221956 A1* | 7/2020 | Tzvieli | G01J 5/0025 |

FOREIGN PATENT DOCUMENTS

| | | |
|---|---|---|
| KR | 20200005986 A | 1/2020 |
| WO | 2021214346 A1 | 10/2021 |

OTHER PUBLICATIONS

Abuzaghleh, et al., "Skincure: An Innovative Smart Phone-Based Application to Assist in Melanoma Early Detection and Prevention," Connecticut, 2015, https://arxiv.org/ftp/arxiv/papers/1501/1501.01075.pdf.

Cerquera-Jaramillo et al., "Visual Features in Alzheimer's Disease: From Basic Mechanisms to Clinical Overview," 2018, Columbia, Hindawi, Neural Plasticity, vol. 2018, pp. 1-21.

Chupin, et al., "Fully Automatic Hippocampus Segmentation and Classification in Alzheimer's Disease and Mild Cognitive Impairment Applied on Data from ADNI," pp. 579-587, 2009, https://www.ncbi.nlm.nih.gov/pmc/articles/PMC2837195/.

Friston, et al., "A Multivariate Analysis of PET Activation Studies," 1996, Human Brain Mapping, Open Access Research, vol. 4, Issue 2, pp. 140-151.

International Search Report and Written Opinion of International Searching Authority for PCT/IB2021/054394, ISA/IL, Jerusalem, Israel, dated Aug. 17, 2021.

Investigacion, et al., "Detecting Eye Diseases Using a Smartphone," 2015, Science Daily, pp. 1-2.

Lim, et al., "The Eye as a Biomarker for Alzheimer's Disease," Frontiers in Neuroscience, Australia, 2016, pp. 1-14.

Martinez-Murcia et al., "Functional Activity Maps Based on Significance Measures and Independent Component Analysis," 2013, Published in final edited form as: Comput Methods Programs Biomed. Jul. 2013; 111(1): 255-268. Published online May 6, 2013. doi: 10.1016/j.cmpb.2013.03.015.

Murcia- Martinez et al., "A Spherical Brain Mapping of MR Images for the Detection of Alzheimer's Disease," Current Alzheimer Research, vol. 13, Issue 5, 2016, pp. 575-588.

Padma, et al., "Segmentation and Classification of Brain CT Images Using Combined Wavelet Statistical Texture Features," Arab J Sci Eng 39, 767-776 (2014). https://doi.org/10.1007/s13369-013-0649-3.

Zhang, et al., "3D Texture Analysis on MRI images of Alzheimer's Disease," Brain Imaging and Behavior 6, 61-69 (2012). https://doi.org/10.1007/s11682-011-9142-3.

Zhang, et al., "Classification of Alzheimer Disease Based on Structural Magnetic Resonance Imaging by Kernel Support Vector Machine Decision Tree," Progress in Electromagnetics Research, vol. 144, pp. 171-184, 2014, CHINA.

Zhang, et al., "Detection of Subjects and Brain Regions Related to Alzheimer's Disease Using 3D MRI Scans Based on Eigenbrain and Machine Learning," 2015, China, https://www.ncbi.nlm.nih.gov/pmc/articles/PMC4451357/.

\* cited by examiner

METHODS FOR REMOTE VISUAL IDENTIFICATION OF CONGESTIVE HEART FAILURES

CROSS-REFERENCE TO RELATED APPLICATIONS

This application is a continuation-in-part of U.S. application Ser. No. 17/649,452 filed on Jan. 31, 2022, now pending, which claims the benefit of U.S. patent application Ser. No. 16/880,683 filed on May 21, 2020, now U.S. Pat. No. 11,276,498. The contents of the above-referenced applications are hereby incorporated by reference.

TECHNICAL FIELD

The present disclosure relates generally to machine vision techniques.

BACKGROUND

The heart is a vital organ in the human body that controls blood circulation, and thus, transport of oxygen and nutrients to various organs and tissues. Heart failure, also referred as congestive heart failure, affects many parts of the body by failing to supply body's demand for oxygen-rich blood. In some cases, blood often backs up and fluid can build up in the lungs and other parts of the body. The severity of heart failure can be defined from class I to class IV according to the classification by the New York Heart Association (NYHA), where zero indicates no signs of heart failure. Extensive progression toward heart failure can cause acute failure that can be life-threatening. To this end, diagnosis of heart failure is advantageous and strongly desired to monitor and maintain physical well beings of patients With appropriate medication and treatment, people who suffer from heart failures can be asymptomatic. However, in absence of such treatments, perhaps due to unawareness of the declined condition, or after strenuous work, decompensation of the heart can occur. Thus, early detection of heart deterioration is critical and highly desired.

However, current diagnostic methods are not readily available during all stages of heart conditions. Current methods are often performed at medical facilities that require in-person doctor visits, and further limited to patients that display certain related symptoms, which could be apparent after extensive progression of the disease. It is highly desired and important to detect deterioration in early stages of disease development for effective treatments. Moreover, current diagnostic methods face challenges to closely and readily track conditions of many different patients as needed. Thus, development and application of alternative diagnosis for identification and treatment of various health conditions, such as heart failure, are desired to allow patients, practitioners, and healthcare payors to enjoy the benefits described herein.

It would, therefore, be advantageous to provide a solution that would overcome the challenges noted above.

SUMMARY

A summary of several example embodiments of the disclosure follows. This summary is provided for the convenience of the reader to provide a basic understanding of such embodiments and does not wholly define the breadth of the disclosure. This summary is not an extensive overview of all contemplated embodiments and is intended to neither identify key or critical elements of all embodiments nor to delineate the scope of any or all aspects. Its sole purpose is to present some concepts of one or more embodiments in a simplified form as a prelude to the more detailed description that is presented later. For convenience, the term "some embodiments" or "certain embodiments" may be used herein to refer to a single embodiment or multiple embodiments of the disclosure.

Certain embodiments disclosed herein include a method for remote diagnosis of a congestive heart failure in humans. The method comprises: receiving a facial image of a patient, wherein the facial image is retrieved from a data store and captured from the patient; extracting, from the facial image, at least one facial feature indicative of a heart condition; classifying the extracted at least one facial feature using a classifier, wherein the classifier maps a plurality of candidate facial features to a plurality of scores indicating a stage of the heart condition; and determining a positive diagnosis and the stage of the heart condition of the patient based on the plurality of scores.

Certain embodiments disclosed herein also include a non-transitory computer readable medium having stored thereon causing a processing circuitry to execute a process, the process comprising: receiving a facial image of a patient, wherein the facial image is retrieved from a data store and captured from the patient; extracting, from the facial image, at least one facial feature indicative of a heart condition; classifying the extracted at least one facial feature using a classifier, wherein the classifier maps a plurality of candidate facial features to a plurality of scores indicating a stage of the heart condition; and determining a positive diagnosis and the stage of the heart condition of the patient based on the plurality of scores.

Certain embodiments disclosed herein also include a system for remote diagnosis of a congestive heart failure in humans. The system comprises a processing circuitry; and a memory, the memory containing instructions that, when executed by the processing circuitry, configure the system to: receive a facial image of a patient, wherein the facial image is retrieved from a data store and captured from the patient; extract, from the facial image, at least one facial feature indicative of a heart condition; classify the extracted at least one facial feature using a classifier, wherein the classifier maps a plurality of candidate facial features to a plurality of scores indicating a stage of the heart condition; and determine a positive diagnosis and the stage of the heart condition of the patient based on the plurality of scores.

BRIEF DESCRIPTION OF THE DRAWINGS

The subject matter disclosed herein is particularly pointed out and distinctly claimed in the claims at the conclusion of the specification. The foregoing and other objects, features, and advantages of the disclosed embodiments will be apparent from the following detailed description taken in conjunction with the accompanying drawings.

DETAILED DESCRIPTION

Figure 1:
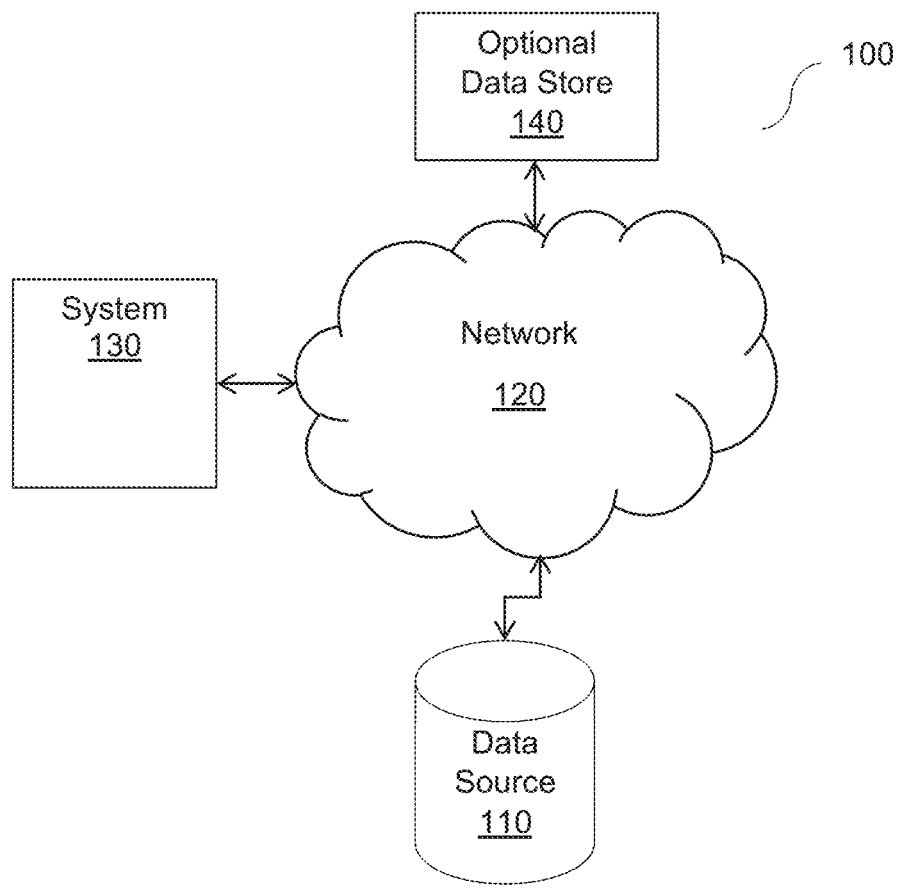
FIG. 1 is a diagram utilized to describe the various embodiments.

It is important to note that the embodiments disclosed herein are only examples of the many advantageous uses of the innovative teachings herein. In general, statements made in the specification of the present application do not necessarily limit any of the various claimed embodiments. Moreover, some statements may apply to some inventive features but not to others. In general, unless otherwise indicated, singular elements may be in plural and vice versa with no loss of generality. In the drawings, like numerals refer to like parts through several views.

The various disclosed embodiments provide a system and method for generating a classifier for remote visual identification of diseases. The classifier is generated for classifying a facial image based on a trained machine learning model that includes facial features that are extracted from facial images. In an embodiment, the classifier is utilized to determine a score for the facial features extracted from captured and retrieved facial images for diagnosis of diseases, such as, but not limited to heart failure, cognitive disorder, and the like, in humans. In an embodiment, the classifier is configured and trained to map a plurality of facial features to a plurality of scores to determine a stage (or extent of progression) of the disease, particularly congestive heart failure conditions.

FIG. 1 is an example diagram 100 utilized to describe the various embodiments. The diagram 100 depicts a data source 110, a diagnosis system 130, and an optional data store 140 communicating over a network 120. The network 120 may be, but is not limited to, a wireless, cellular, or wired network, a local area network (LAN), a wide area network (WAN), a metro area network (MAN), the Internet, the world wide web (WWW), a network similar to those described, and any combination thereof.

In an example embodiment, the data source 110 may be, but is not limited to, a set of facial images, the set including one or more facial images, a streamed video or videos, a data feed from a personal computer, a cell phone, a personal digital assistant (PDA), a surveillance system camera or camcorder, or the like, or a physician's terminal or other device specifically configured for the embodiment. The data stored in each data source 110 may be in a format of structured data, unstructured data, semi-structured data, or a combination thereof.

The diagnosis system 130 (or, simply, the "system" 130) is configured to perform various embodiments disclosed herein. Specifically, the system 130 is configured to implement processes for isolating facial data in images and video. As noted above, all images and video (collectively referred to as "images") received from the data source 110 are processed to isolate facial data. In an embodiment, to allow the isolation of facial data, the system 130 may implement one or more machine learning techniques.

According to the disclosed embodiments, the system 130 may be configured to identify facial features in images. To this end, the system 130 may be configured to identify facial features and expressions in images using neural networks such as, and without limitation, a convolutional neural network (CNN) such as that described with respect to FIG. 5, below.

The system 130 may be utilized to identify and index facial data in images stored in, or otherwise provided by, the data sources 110. To this end, the system 130 is configured to generate a flexible structure to support differently formatted data inputs that represent different types of facial data from the data source 110. In yet another embodiment, the system 130 may be configured to support parallel processing of facial data and, more specifically, parallel analysis of facial data from one or more data sources.

As will be discussed in detail below, the system 130 is configured to implement a process for identifying and categorizing facial data. Actions can be performed in real-time on the received data using a set of predefined commands. In an alternate embodiment, the system 130 may be realized as a separate device such as a local computer, other processing hardware, as a cloud-based distributed service, or a distributed resource.

The system 130 may be implemented as a physical machine, a virtual machine, or a combination thereof. A block diagram of an example depicting a physical machine implementation is discussed below with reference to FIG. 6. A virtual machine may be any virtual software entity, such as a software container, a micro service, a hypervisor, and the like.

The data store 140 may be a relational database or a NoSQL type of database such as, but not limited to, MongoDB, ElasticSearch, and the like. Examples of relational databases may include, but are not limited to, Oracle®, Sybase®, Microsoft SQL Server®, Access®, Ingres®, and the like. In an embodiment, the data store 140 may be a plurality of logical entities residing in the same physical structure. In some configurations, the data store 140 is optional.

According to an embodiment, the data store 140 may be configured to house diagnostic facial data. The diagnostic facial data housed in the data store 140 may include, but is not limited to, data extracted from facial recognition analyses, diagnostic data tags, or a correlative factor expressing the degree to which the diagnostic data tag is accurate for a given extracted facial recognition analysis data set. The diagnostic data tags provide information such as, but is not limited to, whether the data extracted from facial recognition analyses was extracted from a face belonging to a person with a condition (e.g., dementia, heart failure, congestive heart condition, etc.), a risk factor, and the like.

According to an embodiment, the data store 140 may store diagnostic facial data accounting for time and/or age progression. In an embodiment, the facial diagnostic data housed in the data store 140 may include data features accounting for time progression including, but not limited to, multiple facial information data sets for one individual, with each data set tagged with the date of each profile data set and a time-specific diagnostic data tag indicating whether the disease or condition was present at the time the facial information data set was housed in the data store 140.

In an embodiment, the optional data store 140 may be included in the system 130. In an alternate embodiment, the optional data store 140 may be realized as separate components connected directly with the network 120, with the system 130, or with both the system 130 and the network 120. Further, the optional data store 140 may be removed or excluded from various configurations and embodiments as needed.

In an embodiment, the system 130 may be configured to assess the likelihood that facial data, received from the data source 110 via the network 120, contains indicators of disease, including indicators of congestive heart failure. In an embodiment, the system 130 may be further configured to assess the likelihood of disease by extracting, from the facial data set received from the data source 110 via the network 120, a standardized facial data profile, according the system 130. In an embodiment, the system 130 may be configured to assess the likelihood of disease by comparing the standardized facial data profile extracted by the system 130 with standardized facial data profiles received from the data store 140 via the network 120.

It should be noted that the embodiments disclosed herein are not limited to the specific architecture illustrated in FIG. 1, and that other architectures may be equally used without departing from the scope of the disclosed embodiments. Specifically, the system 130 may reside in a cloud computing platform, a datacenter, and the like. The cloud computing platform may be a private cloud, a public cloud, a hybrid cloud, and the like. Moreover, in an embodiment, there may be a plurality of systems operating as a distributed system. Further, the data store 140 may be distributed as well. In some implementations, the system 130 may be an internal component or instance of any of the data sources 110. In an embodiment, the system 130 may include one or more data stores 140, configured to house diagnostic facial data as well as other, like, data.

Figure 2:
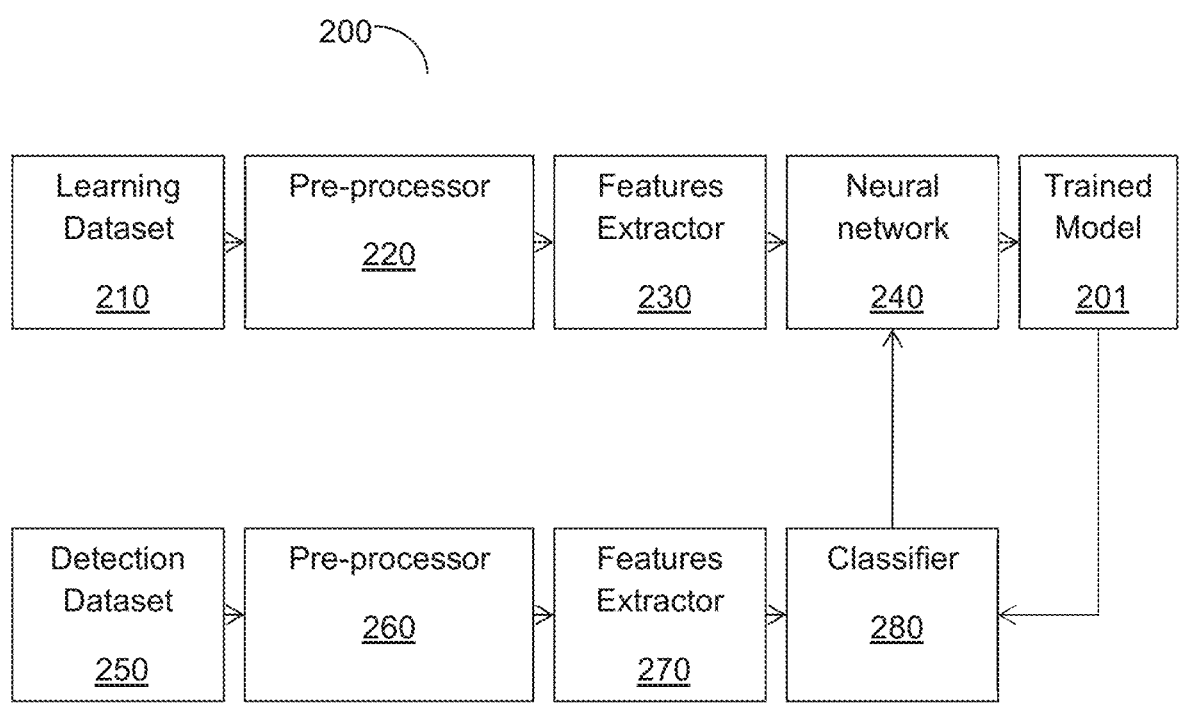
FIG. 2 is an example flow diagram illustrating the generation and application of a supervised model used for classifying a facial image, according to an embodiment.

FIG. 2 is an example flow diagram 200 illustrating the generation and application of a supervised model used for classifying a facial image, according to an embodiment. For sake of simplicity and without limitation of the disclosed embodiments, FIG. 2 will be discussed also with reference to the elements shown in FIG. 1.

The framework depicted in the diagram 200 operates in two phases: learning and detection. In the learning phase, a trained model 201 is generated and trained and, in the detection phase, the trained model 201 is utilized for detection of conditions in association to certain disorders, for example, but not limited to, dementia, congestive heart failure, and the like, in images of people. Such images are received from the data source 110 or from other, similar sources. The trained model 201, in another embodiment, is generated and trained using supervised or semi-supervised machine learning techniques. Images may include video, pictures, video frames, live video feed, and the like. It should be noted that the disclosed embodiments are described with respect to congestive heart failure for illustrative purposes and do not limit the scope of the various disclosed embodiments described herein.

Training and detection may, in an embodiment, occur in cycles. Where a detected facial image is returned to a client and, depending on the feedback received from client indicating whether the detection results are correct or incorrect, the image may be added to the learning dataset 210, and the trained model 201 may be refined accordingly.

In the learning phase, images including at least one human face are received from sources such as the data source 110 and other sources. The received images are aggregated and saved as a learning dataset 210. The aggregation of images may be for a predefined time window (e.g., all images received from the data source 110 during a one-hour time window) or as specified by a user, operator, or predefined scheduling program.

The learning dataset 210 may include images of patients with confirmed congestive heart failure diagnoses, patients confirmed to be congestive heart failure-free, patients with unknown diagnoses, patients with no known diagnoses, and any combination thereof, further including the patients' New York Heart Association (NYHE) scores or other indicators of congestive heart failure status. Further, the learning dataset 210 may include images of patients sampled at various periods, providing time-progression data for patients appearing in images taken or recorded across multiple time periods. In a further embodiment, the images of patients may be sampled during different patient condition statuses, for example but is not limited to, a well-treated condition vs. a severely symptomatic condition, and the like. The inclusion of patient examples at different times and the inclusion of samples from patients with varying congestive heart failure statuses, may allow subsequent analysis of congestive heart failure diagnoses in additional patients, and may allow for differentiation between the visible effects of congestive heart failure and the visible effects of aging.

The learning dataset 210 is input into a pre-processor 220 configured to filter out "noisy" inputs. The pre-processor 220 may be configured to normalize or otherwise adjust images for evaluation and comparison. The pre-processor 220 may standardize the images received from the learning dataset by adjusting image features such as, as examples and without limitation, size, resolution, compression, color, other, like, features, and any combination thereof.

The preprocessed images are fed into a feature extractor 230 configured to extract a set of features representing a human face. In an embodiment, the feature extractor 230 may be configured to identify facial features including, as examples, and without limitation, eyes, lips, cheeks, noses, faces generally, and other, like, features. Facial features may be identified and extracted using techniques from the domain of facial recognition computing, such as landmark analysis, whereby features are identified based on geometry, i.e., recognizing an ellipse-like shape as an eye, or based on comparison to sample or template faces. The extraction of facial features by the feature extractor 230 may include some or all of the processes, methods, elements, or aspects described with respect to S330 of FIG. 3, below.

In an embodiment, the feature extractor 230 may be configured to automatically detect and identify additional facial features in any image included in the dataset. Those features may be extracted explicitly or as part of the model training phase.

In an additional embodiment, the feature extractor 230 may apply genetic algorithm methods, wherein a first facial feature, such as the eyes, are detected, and the remaining feature regions, including those regions adjacent to or containing the first facial feature, are generated based on a predefined genetic algorithm.

The facial features identified and extracted by the feature extractor 230 may allow for the training of a learning model based on the features extracted. In addition to the extracted features, relationships between the features extracted may provide relevant diagnostic data and may allow for the recognition of common hallmark features in subsequent analyses. As examples, relationships determined based on the extracted features may include the distance between two features, the angle of a given feature relative to a given centerline, the overall size or shape of the face identified, other, like, relationships, and any combination thereof.

In an embodiment, multiple features may be extracted from a given image and may be analyzed to provide diagnostic information, to train a learning system, or both. Further, diagnostic accuracy and learning system training accuracy may be enhanced by the extraction of multiple features from multiple face images included in the learning dataset 210.

The extracted features, reflecting the size, shape, and positioning of various aspects of faces, are fed to the neural network 240. In an embodiment, the neural network 240 may be a deep neural network and may implement a semi-supervised or a supervised machine learning algorithm for analyzing the features and generating, using external supporting data, a trained model 201. Further, the neural network may be combined with, supplemented by, or entirely replaced with other, suitable machine learning algorithms, techniques, and methods. The trained model 201 may provide one or more classification rules or rulesets applicable to the creation of the classifier 280. The classifier 280 may be generated and configured as "ready" where the trained model 201 includes a volume of extracted facial features sufficient to provide consistent, accurate diagnosis. Further, one or more classifiers may be generated including, without limitation, multiple classifiers generated to correspond to, and which may be configured for the diagnosis of, unique types of heart diseases, cognitive disorders, and more. Examples of the semi-supervised machine learning algorithms include, and the algorithm may be based on, deep neural networks, support vector machines (SVM), decision trees, label propagation, local outlier factor, isolation forest, and the like.

The supporting data includes labels of certain features previously identified as facial features, information pertaining to a patient's diagnosis status, information pertaining to the collection of images, or facial features, and other, like, information. For example, supporting data may include labels indicating a patient's known congestive heart failure status, the date on which a given image was taken or recorded, and metadata pertaining to the camera and lighting conditions used to capture the face from which the features are extracted.

The trained model 201, generated by the neural network 240 (or the supervised machine learning algorithm), is used to map or correlate facial images or their features, or both, to labels indicating a binary congestive heart failure status, a congestive heart failure status probability, the time elapsed between images of the same patient, the heart congestion level at time of image of the same patient, and other, like, information. The detected facial features are analyzed during the detection phase.

According to an embodiment, the trained model 201 is generated when the learning dataset 210 labels are at rest and in a controlled environment, such as in a lab. It should be noted that the trained model 201 may be generated and trained based on information received from a plurality of co-located learning dataset 210 labels.

In an embodiment, during the detection phase, images received from the data source 110 are aggregated and saved as a detection dataset 250. The aggregation may be performed as described with respect to the learning dataset 210, above.

The detection dataset 250 is input to the pre-processor 260 which performs preprocessing similar or identical to that applied with respect to the pre-processor 220, as described above. The pre-processed datasets, including facial images from the detection dataset 250, are fed into a feature extractor 270. The feature extraction may include some or all of the aspects or elements of the feature extraction performed with respect to the learning dataset 210 at the feature extractor 230, above.

The set of features extracted at the feature extractor 270 are fed to the classifier 280. The classifier 280 is configured to label the features extracted to provide diagnostic information. The labeling is based on the trained model 201, the facial image, and the features extracted from the images analyzed. In addition to labeling images based on the trained model 201, the classifier 280 may be configured to output one or more diagnostic scores. The diagnostic scores produced by the classifier 280 may indicate the presence of a disease or condition, the likelihood of presence of a disease or condition, and other, like, diagnostic information or diagnostic scores.

The classifier 280 may be configured to output diagnostic scores as in formats including, without limitation, binary results, indicating whether a disease or condition is present via a "yes or no" data point, numerical or percentage results, indicating the likelihood that a disease or condition is present, in other, like, formats, and any combination thereof. The classifier 280 can be implemented using known classifying techniques utilized in supervised or semi-supervised machine learning. For example, the classifier 280 can be implemented as a neural network, a k-nearest neighbors (KNN) model, a gaussian mixture model (GMM), a random forest, manifold learning, decision trees, and the like. The classifier 280 utilizes the trained model 201 generated by the neural network 240. The classifier and the neural network are based on the same machine learning model.

In an embodiment, the labels provided by the classifier 280 may be fed into the neural network 240 to improve or otherwise update the trained model 201.

In an example embodiment, any of the neural network 240 and the classifier 280 can be realized by one or more hardware logic components utilized to process artificial intelligence (AI) tasks, such as a digital signal processors (DSPs), tensor processing units (TPUs), or other AI accelerators.

The datasets 210 and 250 can be stored in a memory, which can be volatile (e.g., RAM, etc.) memory, non-volatile (e.g., ROM, flash memory, etc.) memory, or a combination thereof. Alternatively, or collectively, the datasets 210 and 250 can be stored in a storage, or any other medium which can be used to store the desired information.

Figure 3:
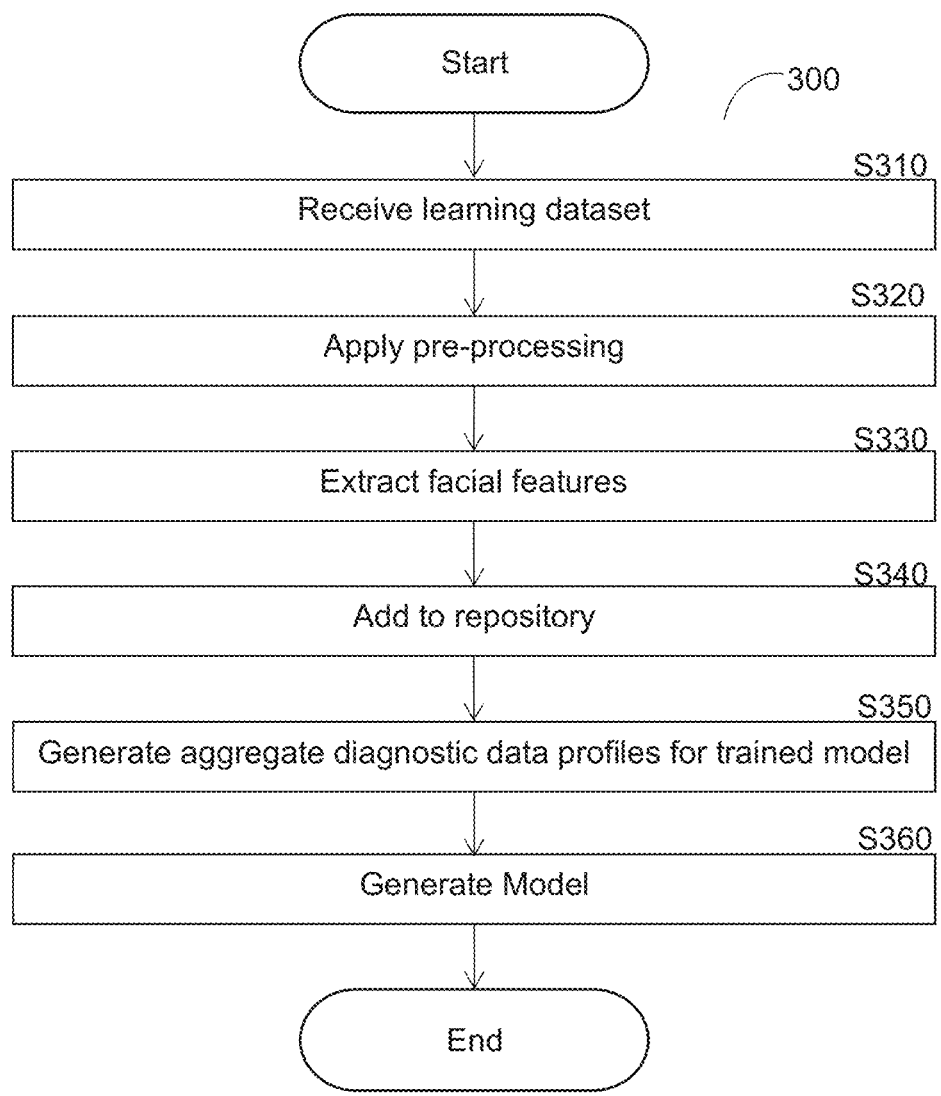
FIG. 3 is a flowchart illustrating the training of a learning model for detection of congestive heart failure based on facial expression according to an embodiment.

FIG. 3 is an example flowchart 300 illustrating the training of a learning model for detection of congestive heart failure based on facial expression. A learning model may be deployed to prepare a system for the execution of a task. By training a learning model on validated, vetted, or otherwise prepared datasets, the system, including the learning model, may be configured to execute a task including analysis of a similar dataset with minimal or no supervision. The method presented herein is described with respect to the detection of heart conditions, specifically congestive heart failure conditions for illustrative purposes. However, it should be noted that the method is not limited to such cardiovascular diseases, and the learning model can be trained and utilized for detection of other diseases or diagnostic conditions such as, but not limited to, cognitive disorders, and more, from facial images.

In an embodiment, the method described with respect to the flowchart 300 may be applied by a feature extractor and neural network, such as the feature extractor 230 and the neural network 240 of FIG. 2, above, to train a diagnostic model, such as the trained model 201 of FIG. 2, above.

In an embodiment, at least one learning dataset is first received at S310. The received learning dataset may include one or more images containing human faces, as well as data labels associated with the images. The received learning dataset may include images of human faces other than the face of the patient for which diagnosis is sought. In an embodiment, the at least one learning dataset necessarily includes a facial image or images from which a facial data profile may be extracted, a data label identifying the subject of the image or images, and a diagnosis label identifying the diseases or conditions which the subject of the image or images is known to possess. Further, the received learning dataset may include facial images and corresponding labels identifying whether the labeled facial image represents a cognitive disorder condition.

In another embodiment, the at least one learning dataset may also include, but is not limited to, a data label identifying the date of the image or images, an age label identifying the age of the subject of the image or images, and the like.

In yet another embodiment, the at least one learning dataset may be received from a physician, physician's assistant, nurse, or other medical practitioner connected with the diagnosis of the subject of the image or images. The learning dataset may be similar, or identical, to the learning dataset 210 of FIG. 2, above.

Subsequently, in an embodiment, the learning dataset may be analyzed to normalize received facial images and identify the contents of the included data labels, using pre-processing methods, at S320. The application of pre-processing techniques at S320 may include normalizing, correcting, or otherwise standardizing the received facial images to reduce or eliminate visual "noise," permitting subsequent feature extraction from the normalized facial images. The application of pre-processing at S320 may include techniques similar or identical to those applied by the pre-processor, 220, of FIG. 2, above.

In an embodiment, the application of pre-processing techniques at S320 may include the identification of the contents of the included data labels by separating data labels from the received facial dataset. In an embodiment, pre-processing analysis of the received dataset may include, but is not limited to, the creation of a unique subject profile or the modification of an existing subject profile.

In an embodiment, pre-processing analysis of the included data labels may include matching the at least one received dataset to existing or newly-created subject profiles based on the contents of data labels including, but not limited to, subject name, social security number, or other unique identifiers.

Next, in an embodiment, the at least one received learning dataset may be analyzed to extract one or more facial features at S330. The extraction of one or more facial features at S330 may include the extraction of at least one learning facial feature indicative of a heart condition. In an embodiment, the facial image or images received as a part of the at least one learning dataset may be analyzed to render the image or images as a combination of numerical values reflecting attributes of the face shown in the image or images, allowing the extraction of the relevant facial feature data from the data describing the face. The techniques used to convert the received image or images into numerical descriptors may include, and are not limited to, recognition of facial geometry by analysis of the size, positions, or shape of facial features including the nose, eyes, cheekbones, and jaw. Furthermore, the techniques used to convert the received image or images into numerical descriptors may also include, but are not limited to, analysis of 3-D images or profiles and recognition and tracking of skin features such as lines, wrinkles, and spots. In addition, the techniques used to convert the received image or images into numerical descriptors may also include, but are not limited to, processing of thermal imaging profiles to identify unique features of the subject's face detectable in thermal spectra. Further, at S330, automatic feature extraction techniques, including landmark analysis, genetic algorithms, and other, like, techniques, including those described with respect to the feature extractor 230 of FIG. 2, above, may be applied to extract facial features.

In an embodiment, the extraction of facial features at S330 may include the application of one or more convolutional neural networks (CNNs), as described with respect to FIG. 5, below, to identify and detect facial expressions and features or include any other supervised methods of feature extraction.

In an embodiment, the methods used to convert the image or images included in the received at least one learning dataset into numerical descriptors may include techniques enabling the analysis of facial expressions. The techniques enabling the analysis of facial expressions may include, but are not limited to, tracking of geometric features, such as the nose, chin, cheekbones, and eyes, or the tracking of surface features such as lines, ridges, and spots, or tension of muscles or skin.

In an embodiment, the methods used to convert the image or images included in the received learning dataset into numerical descriptors may include techniques for the generation of numerical descriptions of the differences arising between images of the same subject at different times. For a received dataset containing images of a subject, where a previous dataset contained images of the same subject, and where the currently received at least one dataset and the previous dataset contain data tags specifying a different date or subject age, the image or images received may be compared with the previous image or images.

In an embodiment, the current and previous image or images may be compared by application of the same techniques for numerical description of facial features. Where a difference in the numerical descriptions of facial attributes arises between the current and previous image or images, the difference in numerical descriptions may be recorded. Where the current or previous image or images is or are associated with a data tag specifying a diagnosed disease or condition, the recorded difference between the numerical descriptors of facial attributes for the current and previous image or images may be applicable to diagnosis of similar diseases or conditions from time-progressed images. Where such changes indicate the progression of a specific disease or condition over time, the relevant time-progressed facial features may be extracted and grouped, categorized, or otherwise organized to retain time-progression information during subsequent processing and analysis.

Subsequently, at S340, the received facial dataset may be archived, and the extracted facial features and associated data labels may be indexed. In an embodiment, the extracted facial features, including generated numerical descriptions of facial attributes, and the associated data tags and optional time-progression profiles may be indexed to a repository for algorithmic and administrative access. In an embodiment, the extracted facial features, including generated numerical descriptions, optional time-progression profiles, and separated data labels, may be indexed for future access. In an embodiment, the extracted facial features may be optimized for storage prior to indexing by techniques including, but not limited to, compression, hashing, and the like. In an embodiment, the extracted facial features may be indexed according to attributes including, but not limited to, numerical descriptors, diagnosis and condition data tags, and the like.

At the optional step, S350, aggregate diagnostic data profiles, as may be included in the trained model, 201, of FIG. 2, above, are generated. As each of the at least one received facial datasets contains a facial image or images, as well as one or more data labels identifying the subject and any of the subject's diagnosed diseases or conditions, the creation of aggregate diagnostic data profiles is possible. In an embodiment, a feature-diagnosis diagnostic data profile may be continuously updated by recomputing the average numerical descriptors of facial features or diagnoses for a given disease or condition upon indexing extracted facial features associated with a data label specifying the given disease or condition. For example, upon indexing extracted facial features associated with a congestive heart condition diagnosis data tag, an aggregate diagnostic data profile may be recomputed by taking various statistical measures including, but not limited to, the mean, the median, the mode, and the like, of the numerical descriptors of each extracted facial feature or set of features tagged with the disease or condition, including the received extracted facial features.

In an embodiment, a feature-probability aggregate diagnostic data profile may be continuously updated by recomputing the likelihood of a given diagnosis based on numerical descriptors of facial features or expressions upon indexing extracted facial features. For example, upon indexing extracted facial features associated with a diagnosis data tag, the numerical descriptors of the subject's facial features or expressions may be compared with the numerical descriptors of other extracted facial data profiles to identify numerical descriptors common to multiple extracted facial features associated with the same disease or condition data label. For example, if eighty percent of subjects diagnosed with a condition have a chin-to-eye separation of more than twice the length of the nose, newly-indexed extracted facial features fitting the same criteria may be matched with an eighty percent likelihood of diagnosis for that disease or condition. Further, in the example, the calculation of likelihood of diagnosis based on extracted numerical descriptors may be continuously updated by factoring newly-indexed extracted facial features, the associated numerical descriptors, and the associated data labels into the determinative criteria.

At S360, one or more trained models are generated. The one or more trained models may be generated in a manner similar or identical to that described with respect to the trained model, 201, of FIG. 2, above. Further, the generation of one or more trained models may include the application of neural network techniques, including deep learning, which may be similar or identical to those described with respect to the neural network, 240, of FIG. 2, above.

Figure 4:
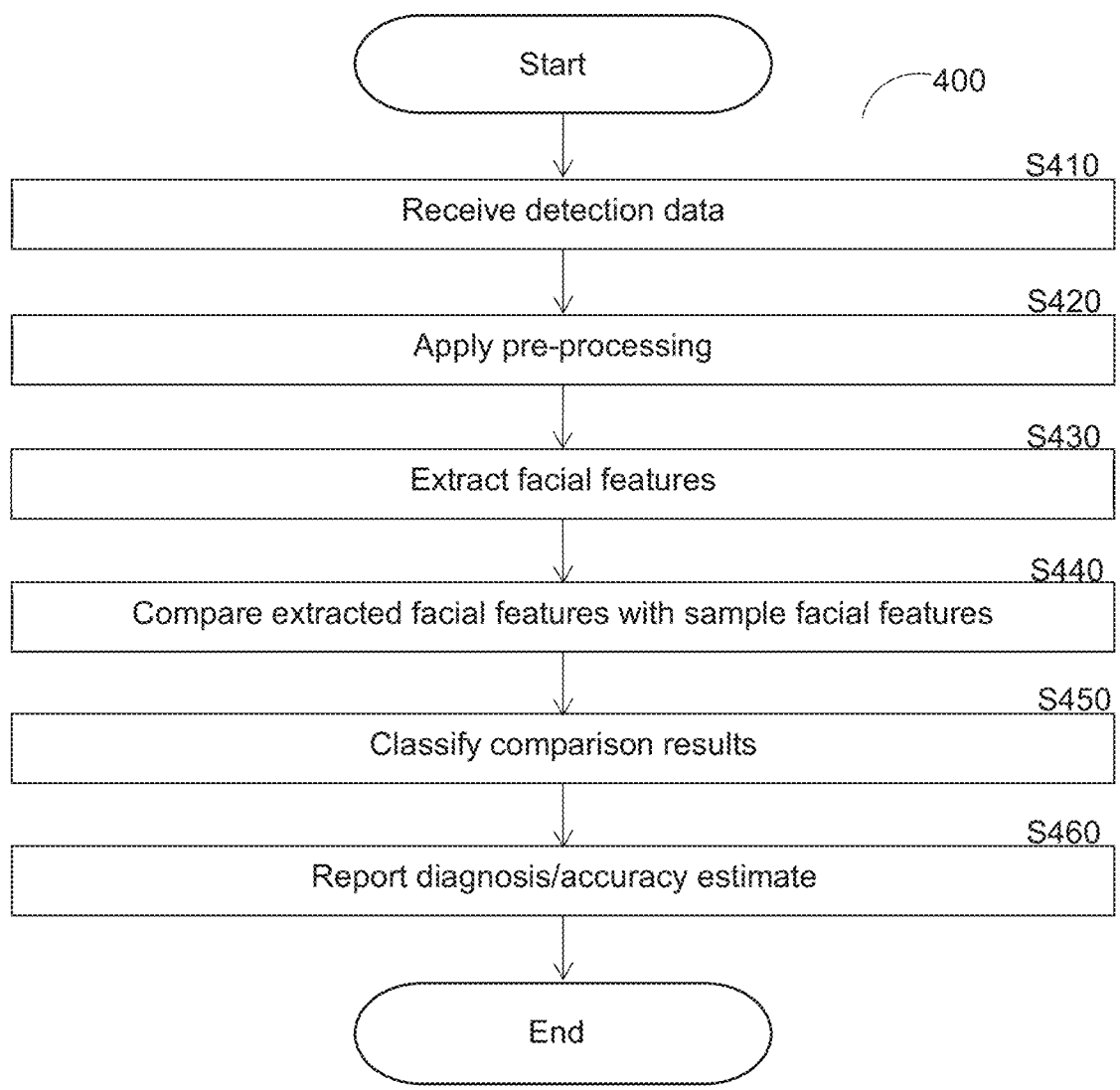
FIG. 4 is a flowchart illustrating the application of the various embodiments to diagnose diseases from facial data.

FIG. 4 is an example flowchart 400 illustrating the application of the various embodiments to a diagnosis of disease from facial data. Such diagnosis, as depicted in the flowchart 400, may occur in the feature extractor 270 and classifier 280 of FIG. 2, above. Diagnosis according to the method described in the flowchart 400 may be applicable to diagnosis of cardiovascular diseases (or heart conditions) including, without limitation, congestive heart failure and other, like, conditions. In an embodiment, the method described in FIG. 4 may be applied to determine a diagnosis of other diseases, for example, cognitive disorders, and the like.

At the outset, in the embodiment, detection data is received at S410 over a network including, without limitation, the network 120 of FIG. 1, above. The received detection data, which may be, without limitation, captured or uploaded at the data source, 110, of FIG. 1, above. The detection dataset includes at least one still image containing a human face. The detection data received may include views of multiple faces, views of the same face from multiple angles, views of the same face in different lightings, or views of the same face obstructed by articles such as, but not limited to, hats, scarves, sunglasses, and the like. Further, the detection dataset may be similar, or identical, to a detection dataset 250 of FIG. 2, above.

At S420, the detection data received at S410 is pre-processed and analyzed to reduce visual noise and detect faces within the detection data. In an embodiment, the system 130 accomplishes the pre-processing of detection data by one or more of several methods. The pre-processing methods applied at S420 may include one or more aspects or elements discussed with respect to the pre-processor, 260, of FIG. 2, above, including pre-processing methods applicable to the reduction of visual noise by normalizing, correcting, or otherwise standardizing facial images in preparation for subsequent feature extraction.

The methods employed in the diagnostic system 130 to pre-process detection data and detect faces in the received detection data include, but are not limited to, convolutional neural network applications, as described with respect to FIG. 5, below, other, like, methods, and any combination thereof. In an embodiment, the accuracy of the algorithm approach may be further improved by normalization of the detected face to correct for uneven lighting and head movements. Finally, in an embodiment, the accuracy of the algorithm approach may be improved by selection of detected faces which possess a high degree of fit in comparison to a set of eigenfaces.

At S430, facial features are extracted from the detection data received at S410 based on the facial features detected at S420. The isolated facial features express the characteristics of the received facial data as an image-independent dataset and may include, but are not limited to, extracted facial expressions, features, and combinations thereof. The extracted facial features may include one or more facial features indicating heart conditions and/or heart diseases. The facial feature parts include, but is not limited to, eyes, lips, cheeks, skin, muscles, and the like, which may be characterized by, for example but not limited to, shape, size, tone, length, color, and more. The extraction of facial features may be achieved by methods including, but not limited to, geometric methods which assess relative facial feature size and placement, statistical methods which compare facial images with templates, three-dimensional analysis, skin-texture mapping, the like, and any combination thereof.

In an embodiment, the extraction of a facial data profile includes the generation of at least one numerical feature describing facial expression. Further, the extraction of facial features at S430 may include some or all aspects, elements, or sub-processes of the facial data extraction step S330 of FIG. 3, above. In addition, the extraction of facial features at S430 may include aspects of the identification and extraction of time-progression facial features, where the extraction of time-progressed facial features is further described with respect to S330 of FIG. 3, above.

At the optional S440, extracted facial features from S430 are compared with sample facial features. The sample facial features are housed in the data store 140 and may contain, without limitation, facial feature information of the same format as the facial features extracted at S430, a data label indicating the date on which the sample facial data profile was generated, a data label indicating the presence of one or more diseases or conditions, and the like. In an embodiment, the comparison of facial features may include the selection of sample facial features which most closely match the extracted facial features, the selection of a sample facial feature which most closely matches a specific attribute or attributes of the extracted facial features, or one or more sample facial features which closely match the extracted facial features based on overall similarity, attribute similarity, or a combination thereof. In an embodiment, the sample facial features may include some or all of the features extracted by the feature extractor 230 of FIG. 2, above, upon extraction of features from the learning dataset 210, also of FIG. 2, above.

In an embodiment, the comparison of extracted facial features with sample facial features may include the construction of eigenfaces from sample facial features and the comparison of extracted facial features with the set of eigenfaces. As the construction of eigenfaces and subsequent expression of extracted facial features in terms of the constructed eigenfaces reduces the processing required versus comparing extracted facial features with individual sample facial features, the construction of eigenfaces, and subsequent comparison, may result in improved processing speed in an embodiment.

At S450, the classification of a disease or condition may be determined. The classification at S450 may include all, some, or none of the outputs generated at the optional S440. Where the optional S440 is omitted or included in part, classification at S450 may include, but is not limited to, the identification of sample facial features matching the extracted facial features, or certain attributes thereof, and the aggregation of the disease or condition data labels for each matching facial feature or set of features. The classification of diseases or conditions may include mapping one or more facial features to a score indicating a stage of cardiovascular health (i.e., heart condition) decline. Further, the classification of diseases or conditions may include assigning one or more scores to one or more extracted facial features, the scores reflecting the current condition of a patient's condition including, without limitation, the progression or level of a diagnosis, such as between early and advanced congestive heart failure conditions. In an embodiment, an extracted facial feature or set of facial features may be classified where a certain percentage of those compared sample facial features include data labels for a certain disease or condition. For example, if ninety percent of top-matched facial feature sets include a congestive heart condition label, a classification including a congestive heart failure diagnosis, as well as a confidence rating for the classification, may be established. The classification of an extracted facial feature or set of facial features as relevant to a disease or condition at S450 may include the generation of a binary "yes or no" classification, a classification certainty score, and the like. In an embodiment, the classification, at S450, of an extracted facial feature or set of facial features relevant to a disease or condition may include features, elements, or aspects similar or identical to those described with respect to the operation of the classifier, 280, of FIG. 2, above. Further, classification of an extracted facial feature or set of facial features at S450 may include the determination of a positive diagnosis of cardiovascular health decline based on one or more scores generated by a classifier, such as the classifier, 280, of FIG. 2, above, upon classification of comparison results. The classifier, such as the classifier 280, of FIG. 2, above, may be generated as described with respect to FIG. 2, above, including by feeding sufficient extracted facial features into a deep neural network, producing the trained model, 201, also of FIG. 2, above.

In an embodiment, the results generated during the classification at S450, including scores, diagnoses, classifications, and the like, may be fed into a neural network, such as the neural network, 240, of FIG. 2, above, for application in the training or refinement of a trained model, such as the trained model, 201, also of FIG. 2, above.

At S460, the classification and confidence rating determined at S450 may be reported. The reporting of the classification determined at S450 may include, but is not limited to, the condition identified, the confidence determined at S450, an identifier tag enabling administrators to verify results, and a list of specialists practicing in areas concerning the condition identified. In an embodiment, the notification may be reported by means including, but not limited to, e-mail, SMS text message, web browser notifications, direct display to the data source 110, direct report to a physician, and other like means.

As noted above, the disclosed method of flowchart 400 can be utilized to determine heart diseases, such as congestive heart failure. The facial features extracted from facial images may include one or more facial features indicating heart conditions and/or heart diseases. Here, the heart conditions suggest decline or dysfunction of the heart that could result in heart diseases, such as heart failure. Such facial features include, but is not limited to, facial color, size, and color of several facial parts such as eyes, lips, cheeks, skin, muscles, and the like, which may be identified by, for example but not limited to, shape, size, tone, length, color, and more. For example, signs of early stages of heart disease may be visible from the shape and color of the cheeks. Discomfort from shortness of breath may be identified in facial features of the nose and/or skin color and shape. In another example, facial skin features may indicate heart conditions through texture, wrinkles, color (e.g., blue or purple), weight gain, and the like. In yet another example, new buildup or growth on facial features (e.g., wax, rash, and the like) may be identified through the extraction of facial features from the facial image, that suggest, for example, unhealthy cholesterol levels.

In an embodiment, classification of conditions include mapping of one or more facial features extracted from the facial images to a score indicating a stage of the heart condition or level of diagnosis. The stage of the heart condition provides information about the current condition of the patient within the progression of heart conditions in association to congestive heart failure, for example, between low risk and high risk of heart failure. The classification further includes labeling of facial images based on a trained model, facial image, and the extracted facial features. In an embodiment, a positive diagnosis, progression, and the stage of the heart condition for the patient, from which the facial image was taken, is determined based on the classification output.

In an embodiment, the trained model (e.g., the trained model 201, FIG. 2) utilized by the classifier (e.g., the classifier 280, FIG. 2) is trained using a learning dataset including facial images at various stages of the heart condition (and disease). It should be understood that for diagnosis of heart diseases, sample facial features, facial images, associated data labels, and the like, are related to heart diseases. As noted above, a classifier may be generated as described with respect to FIG. 2 above, each for a unique type of disorder, for example, but not limited to, cognitive disorder, heart disorder, kidney disorder, and the like, and related diseases.

Figure 5:
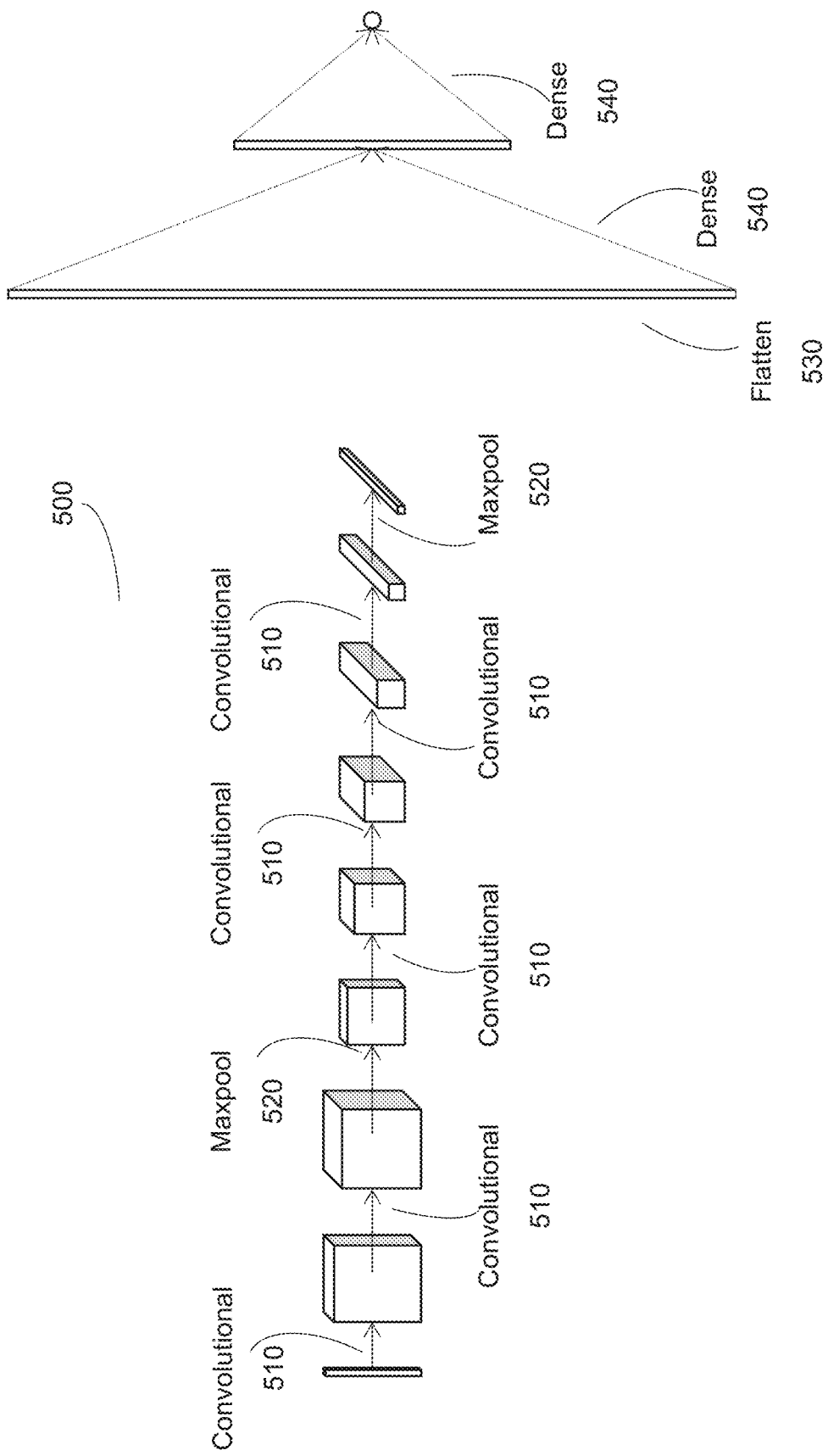
FIG. 5 is a diagram illustrating a sample architectural layout for a convolutional neural network (CNN), according to an embodiment.

FIG. 5 is a diagram 500 illustrating a sample architectural layout for a convolutional neural network (CNN), according to an embodiment. The CNN may be configured to identify and detect facial features and expressions in a received input data feature, such as images and additional surface features, as described above. The CNN may be configured to accept preprocessed face images including, for example and without limitation, in a form that is normalized to a two-dimensional matrix and other features. In an embodiment, the two-dimensional matrix to which the received face image or images are normalized may have a size of, for example, 4096 pixels by 4096 pixels, allowing for capture of fine elements of facial expressions.

The CNN may include multiple convolutional layers 510. Convolutional layers 510 may be configured to reduce multi-dimensional data features into lower-dimensional filtered data maps or other structures. The convolutional layers 510 may process a multi-dimensional data feature by passing a set of filters, alternatively known as kernels, through the span of the data feature, recording the interactions between the filters and the aspects of the data feature as activation maps. In recording the interaction between the filters and the aspects of the data feature, a CNN may learn filters which activate on detection of specific aspects of a data feature.

As each filter applied in the convolutional layer 510 results in a separate activation map, activation maps may be combined for insight into the data feature as a whole. Activation maps may be "stacked" or combined to produce an output volume for the convolutional layer, which may be subsequently processed by similar methods. The output volume may have a similar or identical structure, dimensionality, or both as the received data feature, or the output volume may differ from the received data feature in one or both respects.

As an example of the application of a convolutional layer 510, a three-dimensional data feature, visualized as a cube, may be considered. In the example, the individual filters, visualized as planes the size of a face of the cube, may pass through the cube along the length, thereby fully interacting with every aspect contained within the data feature, and recording the interactions to an activation map. After all the filters pass through the cube, the resulting two-dimensional activation maps may be stacked to produce an output volume describing the data feature based on its interactions with the filters.

In an embodiment, the CNN may be a multi-layered CNN, including a number of layers greater than or equal to four, and including a mix of fully-connected and max-pooling layers 520. In an embodiment, the number of layers included in the CNN, and the associated hyperparameter tuning, may be set or specified with reference to a sample or hold-out dataset. Hyperparameter tuning may describe the modification of the hyperparameters which determine the size and character of the output volume of the convolutional layer 510 as well as dropout rate and other configuration methods. In an embodiment, the hyperparameters modified may include factors affecting connectivity between layered maps which are stacked to form the output volume, factors affecting construction of the output volume in its various dimensions, factors affecting the edges or borders of the output volume, other, like, factors, and any combination thereof.

The CNN may include one or more convolutional layers 510, one or more max-pooling layers 520, other, like, layers, and any combination thereof. Max-pooling layers 520 may reduce the complexity of a received data feature by dividing the received feature into sub-units, each of which may be clustered within the data feature. The max-pooling layer 520 may reduce the complexity of the received data feature by selecting the highest-valued sub-units in each cluster while preserving the arrangement and relationships between the clusters. The selection of the highest-valued sub-units in each cluster may be achieved by noting a metric of interest, by which each sub-unit may be evaluated. The application of max-pooling layers 520 provides for a simplification of the data features processed, enabling greater subsequent processing speeds and reduced processing requirements, and allowing a system to identify and express the important aspects of the received data feature, localized within the feature to preserve significance with respect to other aspects.

In an example, a picture composed of pixels may be divided into a number of clusters, each including multiple pixels. After assigning a color scoring scheme which provides values for each color with, as an example, red being the highest and blue being the lowest, a max-pooling layer may simplify the original image by selecting the highest-scored pixel in each cluster and noting that pixel as having the maximum value for that cluster. By this method, the "reddest" pixel of each portion of the image may be selected.

In an embodiment, a multi-layered network may be deployed to permit abstraction and generalization. The implementation of max-pooling layers 520 and dropout layers may contribute to generalization of a model and the ability to work on new, previously unseen faces.

In an embodiment, dimensionality reduction methods, such as principal component analysis (PCA) and singular value decomposition (SVD), may be applied to map a given problem space into a lower feature space. In addition, dimensionality reduction may be achieved by application of features inherent to one or more applied neural networks, allowing for single-step CNN processing and dimensionality reduction. Dimensionality reduction methods may be applied to reduce the variables considered in facial analysis, allowing execution of methods directed to specific facial features or expressions with reduced runtime, reduced resource requirements, or both. An example of a dimensional reduction is depicted with respect to the flattening 530 and densification 540 shown in the diagram 500.

In the flattening 530 and densification 540 elements included in the example diagram 500, a data feature is "flattened" 530 so that components of the data feature are uniformly accessible, rather than retaining the nested or otherwise-structured formats which the data may include, as received. Following "flattening" 530, the data is "densified" 540, reducing the presence of certain variables in the data feature to enable further processing with greater efficiency. In an embodiment, the dimensional reduction process of flattening 530 and densifying 540 may be repeated multiple times, with the densified data feature being flattened and subsequently densified, again.

Figure 6:
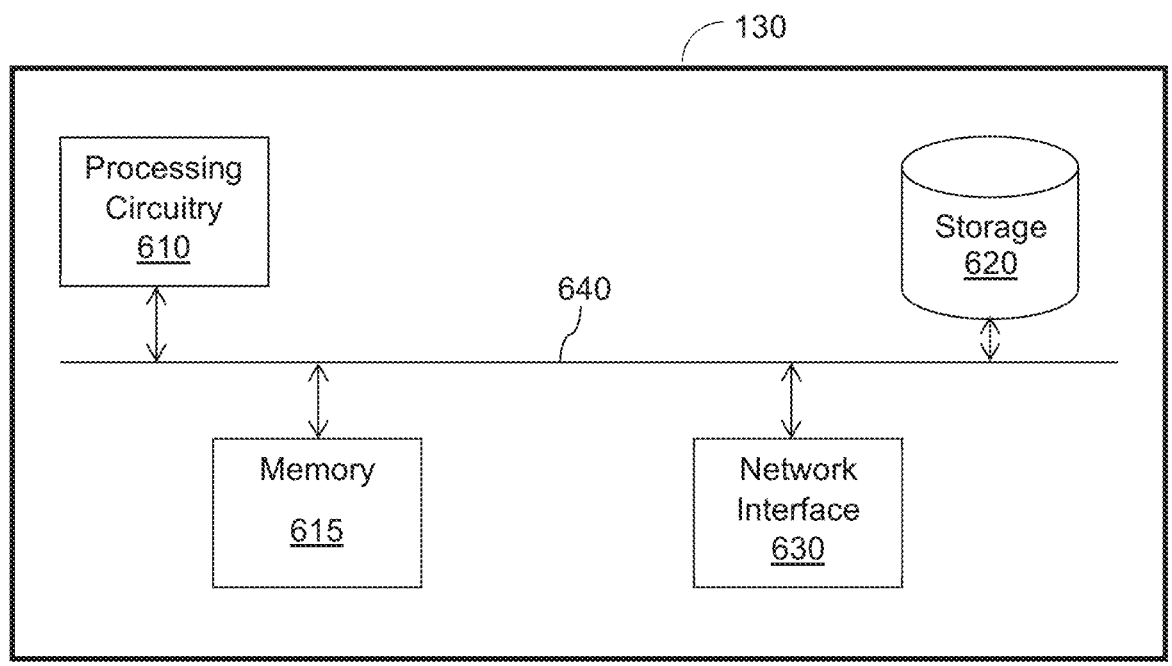
FIG. 6 shows a block diagram of the system implemented according to an embodiment.

FIG. 6 shows an example block diagram of the system 130 implemented according to an embodiment. The system 130 includes a processing circuitry 610 coupled to a memory 615, a storage 620, and a network interface 630. In an embodiment, the components of the system 130 may be communicatively connected via a bus 640.

The processing circuitry 610 may be realized as one or more hardware logic components and circuits. For example, and without limitation, illustrative types of hardware logic components that can be used include field programmable gate arrays (FPGAs), application-specific integrated circuits (ASICs), application-specific standard products (ASSPs), system-on-a-chip systems (SOCs), general-purpose microprocessors, microcontrollers, graphics processing units (GPUs), tensor processing units (TPUs), general-purpose microprocessors, microcontrollers, and digital signal processors (DSPs), and the like, or any other hardware logic components that can perform calculations or other manipulations of information.

The memory 615 may be volatile (e.g., RAM, etc.), non-volatile (e.g., ROM, flash memory, etc.), or a combination thereof. In one configuration, computer readable instructions to implement one or more embodiments disclosed herein may be stored in the storage 620.

In another embodiment, the memory 615 is configured to store software. Software shall be construed broadly to mean any type of instructions, whether referred to as software, firmware, middleware, microcode, hardware description language, or otherwise. Instructions may include code (e.g., in source code format, binary code format, executable code format, or any other suitable format of code). The instructions, when executed by the one or more processors, cause the processing circuitry 610 to perform the various processes described herein.

The storage 620 may be magnetic storage, optical storage, and the like, and may be realized, for example, as flash memory or another memory technology, CD-ROM, Digital Versatile Disks (DVDs), or any other medium which can be used to store the desired information.

The network interface 630 allows the system 130 to communicate with the at least one various data sources (FIG. 1, 110). The embodiments described herein are not limited to the specific architecture illustrated in FIG. 6, and other architectures may be equally used without departing from the scope of the disclosed embodiments.

The embodiments disclosed herein can be utilized to detect other conditions which may present a signature facial feature or features, such as Parkinson's disease, Alzheimer's disease, anxiety, depression, and the like. Where non-congestive heart failure conditions present signature or characteristic facial features, such as recognizable expressions, event-driven changes to expression or other facial features, or time-progressed facial changes, the disclosed embodiments may be appliable to the diagnosis of these conditions.

Where a condition is known to present a signature facial feature or expression which is immediately apparent, requiring no showing of change from a baseline or reference facial feature, the condition may be suitable for diagnosis using methods similar or identical to those described herein. Certain conditions, including conditions manifesting extreme displays of emotions such as anger, fear, joy, and excitement, may be identified by characteristic facial features. In an embodiment, diagnosis of progression-independent conditions, for which no baseline or reference facial image is needed to accurately diagnose the condition, may include extraction of facial features, as described above, in addition to comparison of the extracted features with one or more condition or diagnosis datasets. In an embodiment, the condition or diagnosis datasets used to diagnose progression-independent conditions may include one or more facial images, one or more extracted facial features or sets of extracted facial features, other, like, data, and any combination thereof.

Further, the contents of the condition or diagnosis datasets may be labeled with one or more diseases, diagnoses, or conditions. The condition or diagnosis datasets may be stored in data repositories including, without limitation, the data store, 140, of FIG. 1, above, various user or commercial devices, remote servers, other, like, repositories, and any combination thereof. Where a patient's extracted facial features are similar or identical to those extracted facial features included in the diagnosis or condition datasets, the corresponding label or labels, as well as an associated confidence rating describing the similarity of the labeled facial features to the received facial features, may be returned in a manner similar or identical to that described above.

Further, the embodiments disclosed herein may be applicable to the detection of conditions for which a reference facial profile is required, but for which age-progression is not. As various conditions, such as jaundice and certain rashes, may be detected by observation of visual differences between a patient's current facial profile and a reference or baseline profile, these conditions may be detected in a similar manner. As above, facial features may be extracted from a patient's current and reference facial images and compared to isolate facial feature differences arising between the instant image and the reference image. In an embodiment, the differences isolated may be compared to one or more facial difference datasets, the facial difference datasets including extracted facial feature differences corresponding with certain conditions, as well as associated data labels indicating the condition with which the data is associated. Where a patient's isolated facial feature differences correspond with one or more facial feature differences included in the dataset, the label or labels corresponding with the indicated facial feature differences, as well as an associated confidence rating, may be reported, as described above.

In addition, the disclosed embodiments may be further applicable to the detection of conditions, other than congestive heart failure, which present characteristic facial features across a given time period. Certain conditions displaying characteristic time-progressed facial features may include glaucoma, tooth and gum disease, various skin cancers, and other, like, conditions. As above, time-progressed conditions may be diagnosed by comparison of the facial features extracted from a current image with the facial features extracted from a previous image, and comparison of the differences between the features with a dataset including time-progressed facial feature differences and associated condition diagnosis labels. Time-progressed changes may be detected across one or more sample images, wherein a patient's facial features display characteristic signs of a known condition across images captured at different times. In the example figures, the patient's facial features display time-progressed changes to the cheeks, mouth, eyes, eyebrows, chin, and jaw. In an embodiment, the application of time-progressed facial feature diagnosis may include normalizing the detected facial feature differences with one or more standard aging templates, allowing facial changes due to standard aging to be separated from facial changes due to a disease or condition.

The various embodiments disclosed herein can be implemented as hardware, firmware, software, or any combination thereof. Moreover, the software is preferably implemented as an application program tangibly embodied on a program storage unit or computer readable medium consisting of parts, or of certain devices and/or a combination of devices. The application program may be uploaded to, and executed by, a machine comprising any suitable architecture. Preferably, the machine is implemented on a computer platform having hardware such as one or more central processing units ("CPUs"), a memory, and input/output interfaces. The computer platform may also include an operating system and microinstruction code. The various processes and functions described herein may be either part of the microinstruction code or part of the application program, or any combination thereof, which may be executed by a CPU, whether or not such a computer or processor is explicitly shown. In addition, various other peripheral units may be connected to the computer platform, such as an additional data storage unit and a printing unit. Furthermore, a non-transitory computer readable medium is any computer readable medium except for a transitory propagating signal.

As used herein, the phrase "at least one of" followed by a listing of items means that any of the listed items can be utilized individually, or any combination of two or more of the listed items can be utilized. For example, if a system is described as including "at least one of A, B, and C," the system can include A alone; B alone; C alone; A and B in combination; B and C in combination; A and C in combination; or A, B, and C in combination.

All examples and conditional language recited herein are intended for pedagogical purposes to aid the reader in understanding the principles of the disclosed embodiment and the concepts contributed by the inventor to furthering the art, and are to be construed as being without limitation to such specifically recited examples and conditions. Moreover, all statements herein reciting principles, aspects, and embodiments of the disclosed embodiments, as well as specific examples thereof, are intended to encompass both structural and functional equivalents thereof. Additionally, it is intended that such equivalents include both currently known equivalents as well as equivalents developed in the future, i.e., any elements developed that perform the same function, regardless of structure.

What is claimed is:

1. A method for remote diagnosis of a congestive heart failure in humans, comprising:
receiving a facial image of a patient, wherein the facial image is retrieved from a data store and captured from the patient;
extracting, from the facial image, at least one facial feature indicative of a heart condition, wherein extracting further comprises generating numerical descriptors of facial attributes for the at least one facial feature, wherein the numerical descriptors provide a facial geometry of the at least one facial feature;
classifying the extracted at least one facial feature using a classifier, wherein the classifier maps a plurality of candidate facial features to a plurality of scores indicating a stage of the heart condition; and
determining, using the classifier, a positive diagnosis and the stage of the heart condition of the patient based on the plurality of scores of the plurality of candidate facial features.

2. The method of claim 1, further comprising:
pre-processing of the facial image to standardize the facial image and detect a face within the facial image.

3. The method of claim 1, further comprising:
comparing the at least one facial feature to sample facial features, wherein the sample facial features include data labels associated with respective sample facial features; and
selecting at least one matching sample facial feature that compares substantially closely to the at least one facial feature.

4. The method of claim 1, wherein the classifier is trained to provide a confidence rating for each of the plurality of scores.

5. The method of claim 1, wherein the at least one facial feature indicative of the heart condition is any one of: eyes, lips, skin, ear, forehead, facial muscle tone, size, shape, length, facial color, and cheeks.

6. The method of claim 1, further comprising:
generating the classifier, wherein the classifier is generated for a unique type of heart disease.

7. The method of claim 6, further comprising:
receiving a labeled dataset including a set of facial images, wherein each of the facial images is labeled depending on whether it represents a heart disease;
extracting, from each facial image in the set of facial images, at least one learning facial feature indicative of the heart condition; and
feeding the extracted facial features into a deep neural network to produce a trained model, wherein the classifier is generated and ready when the trained model includes enough facial features processed by the deep neural network.

8. The method of claim 7, wherein the deep neural network implements machine learning techniques including at least: a semi-supervised machine learning algorithm.

9. The method of claim 7, further comprising:
feeding back a score of the determined positive diagnosis to the trained model.

10. The method of claim 1, wherein the facial geometry of the at least one facial feature includes at least one of: size, shape, position, length, color, and relationship between the at least one facial feature.

11. A non-transitory computer readable medium having stored thereon instructions for a processing circuitry to execute the process, the process comprising:
receiving a facial image of a patient, wherein the facial image is retrieved from a data store and captured from the patient;
extracting, from the facial image, at least one facial feature indicative of a heart condition, wherein extracting further comprises generating numerical descriptors of facial attributes for the at least one facial feature, wherein the numerical descriptors provide a facial geometry of the at least one facial feature;
classifying the extracted at least one facial feature using a classifier, wherein the classifier maps a plurality of candidate facial features to a plurality of scores indicating a stage of the heart condition; and
determining, using the classifier, a positive diagnosis and the stage of the heart condition of the patient based on the plurality of scores of the plurality of candidate facial features.

12. A system for remote diagnosis of a congestive heart failure in humans, comprising:
a processing circuitry; and
a memory, the memory containing instructions that, when executed by the processing circuitry, configure the system to:
receive a facial image of a patient, wherein the facial image is retrieved from a data store and captured from the patient;
extract, from the facial image, at least one facial feature indicative of a heart condition, wherein extracting further comprises generating numerical descriptors of facial attributes for the at least one facial feature, wherein the numerical descriptors provide a facial geometry of the at least one facial feature;
classify the extracted at least one facial feature using a classifier, wherein the classifier maps a plurality of candidate facial features to a plurality of scores indicating a stage of the heart condition; and
determine, using the classifier, a positive diagnosis and the stage of the heart condition of the patient based on the plurality of scores of the plurality of candidate facial features.

13. The system of claim 12, wherein the system is further configured to:

pre-process the facial image to standardize the facial image and detect a face within the facial image.

14. The system of claim 12, wherein the system is further configured to:

compare the at least one facial feature to sample facial features, wherein the sample facial features include data labels associated with respective sample facial features; and select at least one matching sample facial feature that compares substantially closely to the at least one facial feature.

15. The system of claim 12, wherein the classifier is trained to provide a confidence rating for each of the plurality of scores.

16. The system of claim 12, wherein the at least one facial feature indicative of the heart condition is any one of: eyes, lips, skin, ear, forehead, facial muscle tone, size, shape, length, facial color, and cheeks.

17. The system of claim 12, wherein the system is further configured to:

generate the classifier, wherein the classifier is generated for a unique type of heart disease.

18. The system of claim 17, wherein the system is further configured to:

receive a labeled dataset including a set of facial images, wherein each of the facial images is labeled depending on whether it represents a heart disease;

extract, from each facial image in the set of facial images, at least one learning facial feature indicative of the heart condition; and feed the extracted facial features into a deep neural network to produce a trained model, wherein the classifier is generated and ready when the trained model includes enough facial features processed by the deep neural network.

19. The system of claim 18, wherein the deep neural network implements machine learning techniques including at least: a semi-supervised machine learning algorithm.

20. The system of claim 18, wherein the system is further configured to:

feedback a score of the determined positive diagnosis to the trained model.

* * * * *